United States Patent [19]

Macovski

[11] 3,965,358

[45] June 22, 1976

[54] CROSS-SECTIONAL IMAGING SYSTEM USING A POLYCHROMATIC X-RAY SOURCE

[76] Inventor: Albert Macovski, 4100 Mackay Drive, Palo Alto, Calif. 94306

[22] Filed: Dec. 6, 1974

[21] Appl. No.: 530,397

[52] U.S. Cl. .................... 250/369; 250/510
[51] Int. Cl.² .............................. G01T 1/20
[58] Field of Search .......... 250/361, 362, 363, 366, 250/369, 510, 360

[56] References Cited
UNITED STATES PATENTS

| | | |
|---|---|---|
| 3,755,672 | 8/1973 | Edholm et al. ............... 250/510 X |
| 3,778,614 | 12/1973 | Hounsfield ..................... 250/362 |
| 3,854,049 | 12/1974 | Mistretta et al. ............ 250/510 X |
| 3,870,885 | 3/1975 | Ammann ..................... 250/366 X |

Primary Examiner—Archie R. Borchelt

[57] ABSTRACT

The transmitted polychromatic x-ray beam in a cross-sectional x-ray imaging system is applied to pulse-height discriminators for energy spectral analysis. Various regions of the energy spectrum are separately counted in order to provide an accurate reconstruction of the cross-sectional density which is independent of the different materials in the path of the transmitted x-ray beam. This same energy spectral information is used to create separate images representing the different materials in the cross section.

12 Claims, 2 Drawing Figures

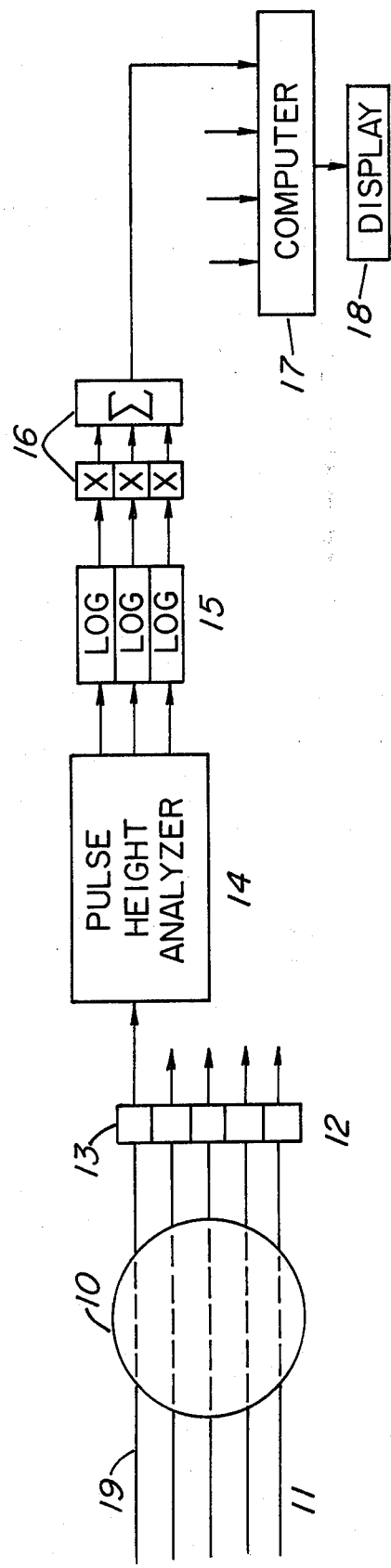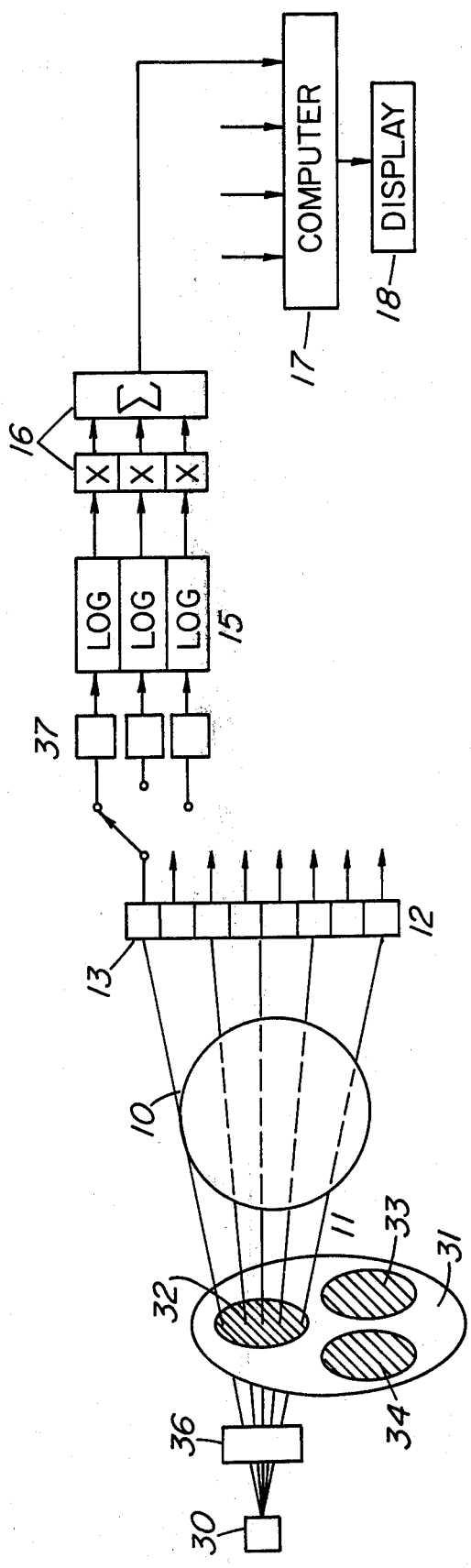

CROSS-SECTIONAL IMAGING SYSTEM USING A POLYCHROMATIC X-RAY SOURCE

BACKGROUND OF THE INVENTION

1. Field of the Invention

This invention relates to cross-sectional x-ray imaging systems. In a primary application the invention relates to the correction for spectral energy shift of a polychromatic x-ray source in cross-sectional imaging systems. In another application the invention relates to obtaining cross-sectional x-ray images of specific materials.

2. Description of Prior Art

Recently two commercial instruments, the EMI and ACTA scanners, have been introduced which provide an accurate cross-sectional image of the brain. This is accomplished by measuring the x-ray projections through the head at 180 different angles and using various mathematical techniques to reconstruct the cross-sectional density. This system is described in a paper by J. Ambrose and G. N. Hounsfield in the British Journal of Radiology, vol. 46, 1973.

One of the biggest sources of inaccuracy of these instruments is the energy spectral shift of the x-ray beam as it traverses the various materials in the cross-sectional slice. The log of the measured transmitted intensity should represent the sum of the linear attenuation coefficients along the x-ray beam. This will be the case if a monoenergetic source is used. These sources, however, have insufficient strength to complete the scan in a reasonable time interval. The use of broadband or polychromatic x-ray sources, which have sufficient strength, results in an accuracy problem since the attenuation coefficients are a function of energy. For example, if a small volume element is traversed by an x-ray beam from two different angles it can provide a different attenuation coefficient at each angle. If the x-ray beam at the different angles goes through different amounts or different types of material it will have a different resultant energy spectrum which in turn results in different attenuation coefficients. The EMI scanner attempts to minimize this problem by using a water bag around the head so that every beam will have the same path length. The relatively uniform geometry of the skull minimuzes the problem of different amounts of bone in the path of the x-ray beam. Thus the EMI scanner is able to achieve reasonably high accuracies while using a broad-band x-ray source. This is described in detail in, "An Evaluation of the Quantitative and Radiation Features of a Scanning X-Ray Transverse Axial Tomograph" by E. C. Mccullough, et.al. in Radiology, vol. 111, June 1974, on pages 709–715.

In many applications the shift of the broad-band energy spectrum is a serious problem. In most areas of the body, outside of the upper region of the head, the beams at different angles encounter significantly different amounts of bone in the path which would result in serious inaccuracies in a reconstructed cross section. The ACTA scanner has discarded the path-length compensation water bag for convenience, although they have not published data on their resultant accuracy.

In addition to obtaining accurate density images, it would be desirable to delineate specific materials within the cross section. This can be accomplished by making x-ray transmission measurements at more than one energy spectrum since different materials have varying attenuations to different regions of the x-ray spectrum. The only published attempt to do this was by J. Ambrose and G. N. Hounsfield in the previously listed paper in the British Journal of Radiology, vol. 46, 1973. In this case two cross-sectional images were made at 100 and 140 Kv. accelerating voltage as the mechanism to change the energy spectrum. Despite the fact that this represents a relatively subtle spectral change, relatively small amounts of iodine were able to be distinguished from calcium densities.

SUMMARY OF THE INVENTION

An object of the invention is to provide apparatus for x-ray cross-sectional imaging using a polychromatic source which can make accurate images of cross-sections having different materials and varying path lengths. A further object of this invention is to provide a method for generating crosssectional images representing the amounts of specific materials.

Briefly, in accordance with the invention, an energy spectrum analysis is made of the x-ray beams transmitted through a cross section of the body at many angles. The logarithms of the outputs at different energies are added with the resultant sums used to reconstruct the cross-sectional densities. The same logarithms of the outputs at different energies are combined in various linear relationships with the resultant reconstruction representing the amounts of specific materials in the cross section.

BRIEF DESCRIPTION OF THE DRAWINGS

For a more complete disclosure of the invention, reference may be made to the following detailed description of several illustrative embodiments thereof which is given in conjunction with the accompanying drawings, of which:

FIG. 1 is a block diagram of an embodiment of the invention using a pulse-height analyzer; and FIG. 2 illustrates an embodiment of the invention using a rotating filter wheel.

DESCRIPTION OF THE PREFERRED EMBODIMENT

An understanding of the broad aspects of the invention may best be had by reference to FIG. 1 of the drawings. A cross-sectional image is being made of object 10 which, for example, can represent some region of the human anatomy such as the head. A sheet beam of polychromatic x-rays 11 is transmitted through the cross section of interest. The transmitted x-rays are detected and measured by detector 12. In order to reconstruct the density of the cross section of object 10 these projections must be measured at a large number of angles as is presently done using the EMI and ACTA scanners which are commercially available. In order to reconstruct the cross section, the information required from each x-ray beam is the line integral or sum of the attenuation coefficients along that beam. Given that information, a wide variety of known techniques can be used to reconstruct the cross-sectional density. These include the Fourier transform method, the convolution method, and the Algebraic Reconstruction Technique (ART). A general discussion of these techniques is given in the paper "Three Methods for Reconstructing Objects From X Rays: A Comparative Study," by G. T. Herman and S. W. Rowland in *Computer Graphics and Image Processing*, vol. 2, 1973, pages 151–178.

One fundamental problem is that of providing the desired information, namely the sum of the attenuation coefficients. The measured output I in each element of detector 12 is given by $$I = \int S(\epsilon)[\exp - \int \mu(z,\epsilon)dz]d\epsilon$$

where $\epsilon$ is the energy level, $S(\epsilon)$ is the energy spectrum of the x-ray source and $\mu(z,\epsilon)$ is the attenuation coefficient which has different values along the beam path indicated by $z$ and also varies with energy. Using this formulation the desired information, namely the line integral of $\mu$, cannot be directly extracted. If the x-ray source is monochromatic with an intensity $I_0$ the measured output becomes $$I = I_0 \exp - \int \mu_0(z)dz$$

where $\mu_0$ is the attenuation coefficient at the monoenergetic energy used. Using logarithms we obtain $$\int \mu_0(z)dz = \ln I_0/I$$

which is the desired quantity needed to reconstruct the cross section of $\mu$ values. The basic problem, using a broad band x-ray source, is that the spectral shift of the spectrum, as it passes through the object, is not known so that the resultant attenuation coefficients are not known. Although a monoenergetic x-ray source solves the problem, this is not a practical solution since available sources of this type are relatively weak. What has been done in the existing commercial scanners is the use of attenuation coefficients at the average energy of the broad band spectrum. Although this leads to error, the resultant errors are minimized in regions, such as the brain, where the geometry is relatively uniform. EMI uses a rotating water bag compensator to maintain constant path length for each beam. Although these techniques reduce the errors, these errors will become quite significant in non-uniform regions of the body such as the chest, abdomen, or extremeties. The high degree of density accuracy required to find tumors will be lost due to the errors inherent in the use of a polychromatic x-ray source. This problem is analyzed in the previously listed paper entitled, "An Evaluation of the Quantitative and Radiation Features of a Scanning X-Ray Transverse Axial Tomograph - (EMI Scanner)," by E. C. McCullough, et.al. in the June 1974 issue of *Radiology*, vol. III, pages 709–715.

A system representing a solution to this problem is shown in FIG. 1. The transmitted beam is measured or counted by detector 12 which can be any x-ray detector such as a scintillating crystal followed by a photodetector or a gaseous proportional counter. The output from each element of the detector, such as element 13, is put through an energy spectral analyzer. This can be a pulse-height analyzer 14 which uses the property that each received photon generates a pulse proportional to its energy. The pulse-height analyzer 14 divides the energy spectrum into a number of pulse height regions. The number of pulses in each spectral region are counted. A number of outputs can be derived each representing the output in a specific region of the energy spectrum. These regions are chosen so that the spectral shift within each region is negligible. Thus, a reconstruction mode with each selected energy region would have negligible errors due to spectral shift and provide a reconstruction essentially identical with that of a monoenergetic source. The problem with this solution is its gross inefficiency in that only a small fraction of the total energy in beam 11 is being used. This not only increases the time of the study but also results in excess radiation of the patron.

The method of FIG. 1 allows all of the energy to be used while compensating for the polychromatic source. The various spectral regions are simultaneously processed to provide the desired output. For example, the output $I_0$ from individual detector 13 in array 12 can be put in summation form providing $$I_0 = \sum_{m=1}^{M} I_m \exp - \sum_{n=1}^{N} \mu_{mn}$$

where $I_m$ is one of the $M$ spectral energy regions of the source and $\mu_{mn}$ is the linear attenuation coefficient of the $n^{th}$ element along the line due to the $m^{th}$ source. The line is being divided into N elements along the x-ray beam. Spectral energy analyzer 14 uses pulse-height analysis to divide the spectral output into M distinct regions. Three are shown as an example in FIG. 1. Following energy selection $I_{0m}$, the individual outputs due to each of the M energy regions are separately available and have the form $$I_{0m} = I_m \exp - \sum_{n=1}^{N} \mu_{mn}$$

Using system 15 a logarithm is taken of $I_{0m}$, the output at each energy band providing the desired sum of the linear attenuation coefficients.

$$\sum_{n=1}^{N} \mu_{mn} = \ln(I_m/I_{0m})$$

This logarithm operation using system 15 can be achieved by a digital or analog circuit and many well-known methods are presently in use. One analog technique makes use of the logarithmic relationship between the current and voltage across a junction diode.

Following the logarithmic operation, a weighted sum is taken of the logs of the various spectral outputs using weighted summing structure 16. In this structure each output is first weighted or multiplied by a predetermined constant with the weighted outputs added. This provides an output signal given by $$\sum_{m=1}^{M} a_m \sum_{n=1}^{N} \mu_{mn} = \sum_{m=1}^{M} a_m \ln(I_m/I_{0m})$$

If the weighting is made uniform by setting all $a_m = 1$, this simply represents the desired sum of the attenuation coefficients at all energies. The various weightings $a_m$ can be used to emphasize or de-emphasize various regions of the energy spectrum if desired. This sum, weighted or unweighted, is applied to computer 17 where one of the previously discussed algorithms is used to reconstruct the effective linear attenuation coefficient at every element. Thus $$\sum_{m} a_m \mu_{mn}$$

will be reconstructed for the $n^{th}$ element using the projections at many angles. The same structure using pulse height analyzer 14, logarithmic structure 15, and weighted summer 16 is used on each detector output of detector 12. The resultant outputs of all of the weighted summations from each detector element are applied to computer 17 to perform the reconstruction. This general system, where a weighted sum of the logarithms of the various spectral outputs are used to compute the cross section, is much more economical and efficient than providing a separate computer reconstruction for each spectral region and then combining the various reconstructed cross sections. The reconstructed cross-sectional information is finally applied to display 18.

Although FIG. 1 indicates a sheet beam geometry using sheet beam 11 and multiple detector 12, the system will operate identically using a scanned pencil beam. In that case the source consists of a single scanning beam 19 and a single scanning detector such as element 13 in the array as is used in the EMI scanner. In this manner the desired information is derived in sequence rather than in parallel. The system is simpler in that a single detector, analyzer, logarithmic structure and weighted summer is used. It does, however, require a longer scan time which makes it relatively unsuitable for studies of moving organs.

In the systems described, a weighted sum is taken of the logarithm of the various spectral outputs so as to create a signal which is representative of the average linear attenuation coefficient. Through a proper choice of spectral regions, using different weightings, the same system can be used to represent the amount of specific materials in the cross section of interest. This has great significance in many applications. In medical diagnosis this system can be used to image administered materials, such as iodine, which are selectively taken up in diseased areas such as tumors.

Each elemental volume in the cross section is assumed to be composed of P known materials. Thus the linear attenuation coefficient of each element in the cross section $\mu_{mn}$ can be given by $$\mu_{mn} = \sum_{p=1}^{P} \sigma_{mp} \rho_{np}$$

where $\sigma_{mp}$ is the mass absorption coefficient of the $p^{th}$ material at the $m^{th}$ energy region, and $\rho_{np}$ is the concentration or density of the $p^{th}$ material in element n in mass per unit volume. It is this latter quantity $\rho_{np}$ which it is desired to calculate, reconstruct, and display for particular materials $p$ since it directly indicates the amount of the material.

The solution to this problem is essentially that of basic linear algebra. If P materials are present in the cross section, the number of spectral regions M to isolate individual materials is at least P. A further requirement is that the measurements, which provide $\mu_{mn}$ values, must be linearly independent. Therefore the spectral regions should be chosen so that the various materials exhibit different behavior. For example, in separating iodine from soft tissue spectral regions can be chosen on either side of the iodine K absorption edge. Similarly, in separating calcium from soft tissue, spectral regions can be chosen where the attenuation due to soft tissue is primarily Compton scattering while that due to calcium is primarily photoelectric absorption.

The basic mathematics involves the solution of P = M simultaneous equations. The solution for $\rho_{np}$ involves a number of terms which consist of functions of $\sigma_{mp}$ multiplying values of $\mu_{mn}$. Since the values of $\sigma_{mp}$ are known from the information on the materials present, these functions are used to weight the measured values of $\mu_{mn}$. As an illustrative example, consider a cross section having two materials where measurements are made at two energy spectra. The measured linear attenuation coefficients are given by $$\mu_{1n} = \sigma_{11}\rho_{n1} + \sigma_{12}\rho_{n2}$$

and $$\mu_{2n} = \sigma_{21}\rho_{n1} + \sigma_{22}\rho_{n2}$$

where $\rho_{n1}$ and $\rho_{n2}$ are the concentrations of materials one and two, while $\sigma_{12}$ is the mass attenuation coefficient of material two at energy spectrum one. Solving these equations for the concentration of material one we obtain $$\rho_{n1} = \left(\frac{\sigma_{22}}{\sigma_{22}\sigma_{11} - \sigma_{12}\sigma_{21}}\right)\mu_{1n} + \left(\frac{-\sigma_{12}}{\sigma_{22}\sigma_{11} - \sigma_{12}\sigma_{21}}\right)\mu_{2n}$$

The expressions in the parentheses, which can be positive or negative, become the weights in weighted summing system 15 in a system with two spectral regions. These weighting factors will result in a reconstruction of the desired valvues of $\rho_{n1}$ at each element in the cross section. The outputs of logarithmic structure 15 will be $$\sum_{n=1}^{N} \mu_{1n}$$

and $$\sum_{n=1}^{N} \mu_{2n}$$

respectively. These, when weighted as indicated by the functions of the mass attenuation coefficients in parentheses will result in the desired reconstruction of a specific material. In essence, the weightings cause cancellation of the two terms in regions where material one is not present so that the output indicates only the presence of material one. This output, as before, goes to reconstruction computer 17 and is displayed on 18.

In the more general case P materials are present in each volume element so that at least M P independent spectral measurements are required. The resultant equations take the form $$\mu_{1n} = \sigma_{11}\rho_{n1} + \ldots\ldots + \sigma_{1P}\rho_{nP}$$
$$\mu_{2n} = \sigma_{21}\rho_{n1} + \ldots\ldots + \sigma_{2P}\rho_{nP}$$
$$\vdots$$
$$\mu_{Mn} = \sigma_{M1}\rho_{n1} + \ldots\ldots + \sigma_{MP}\rho_{nP}$$

These can be simplified using the matrix form $$U = SC$$

where U is a column vector representing the various M values of $\mu_{mm}$, C is a column vector representing the various P values of $\rho_{np}$, and S is a MXP matrix of $\sigma_{mp}$ values where the $m$ values of each row indicate the energy spectrum and the $p$ values of each column indicate the specific material. The solution to this problem is obtained by clasical matrix inversion as given by $$C = S^{-1}U$$

where $S^{-1}$ is the inverse of S. For this to be nonsingular the determinant of S, $|S|$, will have to be non-zero which implies linear independence of the $\sigma_{mp}$ values. Thus, assuming the $\sigma_{mp}$ values are properly chosen in independent regions of the energy spectrum, the weights in weighted summing system 15 for material p will be given by the values of the $p^{th}$ row of $S^{-1}$.

The various values of $\sigma_{mp}$ can be determined experimentally by measuring the transmission of the p materials to the various $m$ energy spectra. They can also be calculated using the relationship $$\sigma_{mp} = \frac{\int X_m(E)\sigma_p(E)dE}{\int X_m(E)dE}$$

where $x_m(E)$ is the $m^{th}$ energy spectrum and $\sigma_p(E)$ is the tabulated Energy-dependent mass adsorption coefficient of the $p^{th}$ material. These are available in most physics handbooks.

Often integrating type of detector systems are used which are not capable of pulse-height analysis. Whenever the count rate greatly exceeds the response time of the detector, an integrating approach is used as in the EMI scanner. In systems of this type spectral analysis can be achieved by sequential filtering rather than pulse-height analysis. A system of this type is illustrated in FIG. 2. A polychromatic x-ray source 30 is collimated into sheet beam 11 using collimator 36. This collimator can be a pair of lead blocks which stop all x-rays other than those passing through the gap between them. This is the same type of source used in the system shown in FIG. 1. A rotating filter wheel 31 is placed in the path of the beam. A sequence of materials 32, 33, and 34 are placed in front of the beam. These provide spectral filtering of the beam whereby certain energy regions are attenuated and others are transmitted. For example, relatively low atomic number materials such as aluminum and copper can be used to attenuate the lower energy regions. In addition, higher atomic number materials such as iodine and tantalum can be used to provide absorption at specific x-ray spectral regions in the vicinity of their K absorption edges.

At each element in detector array 12, such as element 13 as shown, a multipole switch 35 is used. Since the various spectral outputs occur in sequence, switch 35 connects each detector element output to storage device 37 where the outputs due to each filtered spectrum are stored. This can be a digital store or an analog device such as a capacitor. The stored outputs are then treated exactly like the output of the pulse-height analyzer 14 in FIG. 1. The logarithms are taken using 15, a weighted sum is taken by 16 which along with the outputs of the other elements is applied to reconstruction computer 17 and displayed on 18. The weighted summing system 15 can either have all positive weights such as unity for reconstructing a representation of the linear attenuation coefficients or, as previously described, can be the required positive and negative weights for representing the amounts of a specific material.

What is claimed is:

1. An improved cross-sectionsl imaging apparatus of the type wherein a polychromatic x-ray beam is projected through a cross-section of an object at a plurality of angles and wherein the resultant transmitted beam is detected and applied to a reconstruction computer where the detected transmission data is used to reconstruct the density of the cross-section and the reconstructed image information is applied to a display, wherein the improvement comprises:
   means for detecting a plurality of x-ray transmission signals representing the intensity of different energy spectra of the transmitted polychromatic x-ray beam;
   means for deriving the logarithm of each of the x-ray transmission signals; and
   means for deriving a weighted sum of each of the logarithms of the x-ray transmission signals and applying the weighted sum signal to the reconstruction computer.

2. Apparatus as recited in claim 1 wherein the means for detecting a plurality of x-ray transmission signals at different energy spectra includes an x-ray detector which generates a pulse whose amplitude is proportional to the received x-ray energy, connected to a pulse-height analyzer which provides output signals representing different pulse-height intervals whereby each output signal corresponds to an x-ray transmission signal in a specific energy spectrum.

3. Apparatus as recited in claim 2 wherein the x-ray detector is a scintillating crystal followed by a photomultiplier.

4. Apparatus as recited in claim 3 wherein the x-ray detector is a gasesous proportional counter.

5. Apparatus as recited in claim 1 wherein the polychromatic x-ray beam is a sheet beam covering the cross section and the detecting means is an array of x-ray detectors for simultaneously detecting each region of the resultant transmitted bean.

6. Apparatus as recited in claim 1 wherein the means for detecting a plurality of x -ray transmission signals at different energy spectra includes means for sequentially inserting a plurality of x-ray spectral filters in the polychromatic x-ray beam and an x-ray detector positioned in the transmitted beam whose output represents the intensity corresponding to each filtered region of the x-ray spectrum.

7. Apparatus as recited in claim 6 including a plurality of storage devices and means for switching the output of the x-ray detector to each storage device synchronously with the sequential inserting of x-ray spectral filters whereby the output of the storage devices corresponds to the intensity of the filtered regions of the transmitted x-ray spectra and is thus the plurality of x-ray transmission signals.

8. Apparatus as recited in claim 1 wherein the means for deriving the weighted sum of each of the logarithms of the x-ray transmission signals includes a plurality of multipliers each having a constant factor which multiplies each of the logarithms of the x-ray transmission signals and an adder which addes the outputs of the multipliers.

9. Apparatus as recited in claim 8 wherein the values of the constant factors are all positive whereby the reconstructed image represents the density of the cross section.

10. Apparatus as recited in claim 9 wherein the values of the constant factors are all unity whereby the reconstructed image represents the unweighted density of the cross section for the polychromatic spectrum of the x-ray beam.

11. Apparatus as recited in claim 8 wherein the constant factors have both postive and negative values so that the reconstructed image represents the amount of a specific material in the cross section.

12. Apparatus as recited in claim 11 wherein the constant factors are the values of a row of the inverse of the mass absorption coefficient matrix whose column values represent the different materials present in the cross section and whose row values represent the different energy spectra used wherby the reconstructed image represents the material corresponding to the same row of the column vector of the materials present.

* * * * *